United States Patent [19]

Axen

[11] 4,056,556

[45] Nov. 1, 1977

[54] 2,2-DIFLUORO-16-PHENOXY-PGE$_2$ ANALOGS

[75] Inventor: Udo F. Axen, Plainwell, Mich.

[73] Assignee: The Upjohn Company, Kalamazoo, Mich.

[21] Appl. No.: 724,153

[22] Filed: Sept. 17, 1976

Related U.S. Application Data

[62] Division of Ser. No. 552,708, Feb. 25, 1975, Pat. No. 4,001,300.

[51] Int. Cl.$^2$ ............................................. C07C 65/22
[52] U.S. Cl. .................................. 560/53; 260/520 B
[58] Field of Search ........................ 260/473 A, 520 B

[56] References Cited

U.S. PATENT DOCUMENTS 3,775,462  11/1973  Axen ................................ 260/468 D

FOREIGN PATENT DOCUMENTS

| | | |
|---|---|---|
| 1,282,661 | 7/1972 | United Kingdom ............ 260/473 A |
| 1,282,662 | 7/1972 | United Kingdom ............ 260/473 A |
| 1,282,663 | 7/1972 | United Kingdom ............ 260/473 A |

*Primary Examiner*—Paul J. Killos
*Attorney, Agent, or Firm*—Robert A. Armitage

[57] ABSTRACT

2,2-Difluoro prostaglandin E, F$_\alpha$, F$_\beta$, A, and B analog are disclosed with intermediates and with processes for making them. These compounds differ from the prostaglandins in that they have two fluoro atoms at the C-2 position in place of the two hydrogen atoms at C-2 in the prostaglandins. These compounds are useful for a variety of pharmacological purposes, including anti-ulcer, inhibition of platelet aggregation, increase in nasal patency, labor induction at term, and wound healing.

58 Claims, No Drawings

2,2-DIFLUORO-16-PHENOXY-PGE$_2$ ANALOGS

The present application is a divisional application of Ser. No. 552,708, filed Feb. 25, 1975, now issued as U.S. Pat. No. 4,001,300, on Jan. 4, 1977.

The present invention relates to prostaglandin analogs for which the essential material constituting a disclosure therefor is incorporated by reference here from U.S. Pat. No. 4,001,300, issued Jan. 4, 1977.

I claim:

1. A compound of the formula

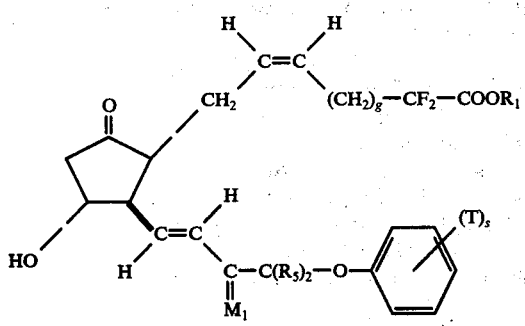

or a mixture comprising that compound and the enantiomer thereof, wherein g is 2 to 4, inclusive;
wherein M$_1$ is

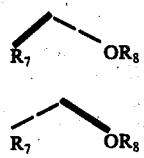

wherein R$_7$ and R$_8$ are hydrogen or methyl, with the proviso that one of R$_7$ or R$_8$ is methyl only when the other is hydrogen;

wherein T is alkyl of one to 3 carbon atoms, inclusive, fluoro, chloro, trifluoromethyl, or —OR$_4$ wherein R$_4$ is alkyl of one to 3 carbon atoms, inclusive, and wherein s is zero, one, 2, or 3, with the proviso that not more than two T's are other than alkyl;

wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro, alkyl of one to 4 carbon atoms, inclusive, or a pharmacologically acceptable cation,

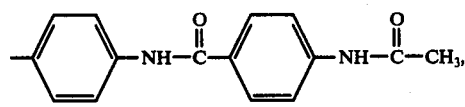

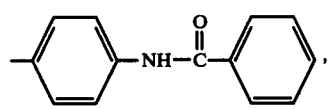

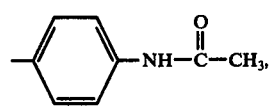

-continued

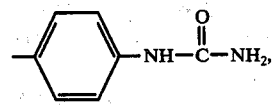

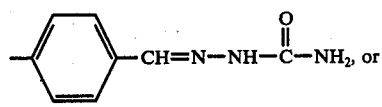

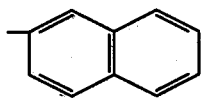

; and wherein R$_5$ is hydrogen or methyl, with the proviso that R$_5$ is methyl only when R$_7$ and R$_8$ are both hydrogen.

2. A compound according to claim 1, wherein M$_1$ is

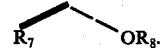

3. A compound according to claim 2, wherein g is 2.

4. A compound according to claim 3, wherein s is 0 or s is one and T is chloro, fluoro, or trifluoromethyl.

5. A compound according to claim 4 wherein R$_7$ is methyl.

6. A compound according to claim 5, wherein s is 1 and T is trifluoromethyl.

7. 2,2-Difluoro-15-methyl-16-(m-trifluoromethylphenoxy)-17,18,19,20-tetranor-PGE$_2$, a compound according to claim 6, wherein R$_1$ is hydrogen.

8. 2,2-Difluoro-15-methyl-16-(m-trifluoromethylphenoxy)-17,18,19,20-tetranor-PGE$_2$, methyl ester, a compound according to claim 6, wherein R$_1$ is methyl.

9. A compound according to claim 5, wherein s is 1 and T is fluoro.

10. 2,2-Difluoro-15-methyl-16-(p-fluorophenoxy)-17,18,19,20-tetranor-PGE$_2$, a compound according to claim 9, wherein R$_1$ is hydrogen.

11. 2,2-Difluoro-15-methyl-16-(p-fluorophenoxy)-17,18,19,20-tetranor-PGE$_2$, methyl ester, a compound according to claim 9, wherein R$_1$ is methyl.

12. A compound according to claim 5, wherein s is one and T is chloro.

13. 2,2-Difluoro-15-methyl-16-(p-chlorophenoxy)-17,18,19,20-tetranor-PGE$_2$, a compound according to claim 12, wherein R$_1$ is hydrogen.

14. 2,2-Difluoro-15-methyl-16-(p-chlorophenoxy)-17,18,19,20-tetranor-PGE$_2$, methyl ester, a compound according to claim 12, wherein R$_1$ is methyl.

15. A compound according to claim 5, wherein s is 0.

16. 2,2-Difluoro-15-methyl-16phenoxy-17,18,19,20-tetranor-PGE$_2$, a compound according to claim 15, wherein R$_1$ is hydrogen.

17. 2,2-Difluoro-15-methyl-16-phenoxy-17,18,19,20-tetranor-PGE$_2$, methyl ester, a compound according to claim 15, wherein R$_1$ is methyl.

18. A compound according to claim 4, wherein R$_8$ is methyl.

19. A compound according to claim 18, wherein s is one, and T is trifluoromethyl.

20. 2,2-Difluoro-16-(m-trifluoromethylphenoxy)-17,18,19,20-tetranor-PGE$_2$, 15-methyl ether, a compound according to claim 19, wherein R$_1$ is hydrogen.

21. 2,2-Difluoro-16-(m-trifluoromethylphenoxy)-17,18,19,20-tetranor-PGE$_2$, 15-methyl ether, methyl ester, a compound according to claim 19, wherein R$_1$ is methyl.

22. A compound according to claim 18, wherein T is fluoro.

23. 2,2-Difluoro-16-(p-fluorophenoxy)-17,18,19,20-tetranor-PGE$_2$, 15-methyl ether, a compound according to claim 22, wherein R$_1$ is hydrogen.

24. 2,2-Difluoro-16-(p-fluorophenoxy)-17,18,19,20-tetranor-PGE$_2$, 15-methyl ether, methyl ester, a compound according to claim 22, wherein R$_1$ is methyl.

25. A compound according to claim 18, wherein s is one and T is chloro.

26. 2,2-Difluoro-16-(p-chlorophenoxy)-17,18,19,20-tetranor-PGE$_2$, 15-methyl ether, methyl ester, a compound according to claim 25, wherein R$_1$ is hydrogen.

27. 2,2-Difluoro-16-(p-chlorophenoxy)-17,18,19,20-tetranor-PGE$_2$, 15-methyl ether, methyl ester, a compound according to claim 25, wherein R$_1$ is methyl.

28. A compound according to claim 18, wherein s is 0.

29. 2,2-Difluoro-16-phenoxy-17,18,19,20-tetranor-PGE$_2$, 15-methyl ether, a compound according to claim 28, wherein R$_1$ is hydrogen.

30. 2,2-Difluoro-16-phenoxy-17,18,19,20-tetranor-PGE$_2$, 15-methyl ether, methyl ester, a compound according to claim 28, wherein R$_1$ is methyl.

31. A compound according to claim 4, wherein R$_7$ and R$_8$ are hydrogen.

32. A compound according to claim 31, wherein R$_5$ is methyl.

33. A compound according to claim 32, wherein s is one and T is trifluoromethyl.

34. 2,2-Difluoro-16-methyl-16-(m-trifluoromethylphenoxy)-18,19,20-trinor-PGE$_2$, a compound according to claim 33, wherein R$_1$ is hydrogen.

35. 2,2-Difluoro-16-methyl-16-(m-trifluoromethylphenoxy)-18,19,20-trinor-PGE$_2$, methyl ester, a compound according to claim 33, wherein R$_1$ is methyl.

36. A compound according to claim 32, wherein s is one and T is fluoro.

37. 2,2-Difluoro-16-methyl-16-(p-fluorophenoxy)-18,19,20-trinor-PGE$_2$, a compound according to claim 36, wherein R$_1$ is hydrogen.

38. 2,2-Difluoro-16-methyl-16-(p-fluorophenoxy)-18,19,20-trinor-PGE$_2$, methyl ester, a compound according to claim 36, wherein R$_1$ is methyl.

39. A compound according to claim 32, wherein s is one and T is chloro.

40. 2,2-Difluoro-16methyl-16-(p-chlorophenoxy)-18,19,20-trinor-PGE$_2$, a compound according to claim 39, wherein R$_1$ is hydrogen.

41. 2,2-Difluoro-16-methyl-16-(p-chlorophenoxy)-18,19,20-trinor-PGE$_2$, methyl ester, a compound according to claim 39, wherein R$_1$ is methyl.

42. A compound according to claim 32, wherein s is 0.

43. 2,2-Difluoro-16-methyl-16-phenoxy-18,19,20-trinor-PGE$_2$, methyl ester, a compound according to claim 42, wherein R$_1$ is methyl.

44. 2,2-Difluoro-16-methyl-16-phenoxy-18,19,20-trinor-PGE$_2$, methyl ester, a compound according to claim 42, wherein R$_1$ is methyl.

45. A compound according to claim 31, wherein R$_5$ is hydrogen.

46. A compound according to claim 45, wherein s is one and T is trifluoromethyl.

47. 2,2-Difluoro-16-(m-trifluoromethylphenoxy)-17,18,19,20tetranor-PGE$_2$, a compound according to claim 46, wherein R$_1$ is hydrogen.

48. 2,2-Difluoro-16-(m-trifluoromethylphenoxy)-17,18,19,20-tetranor-PGE$_2$, methyl ester, a compound according to claim 46, wherein R$_1$ is methyl.

49. A compound according to claim 45, wherein s is one and T is fluoro.

50. 2,2-Difluoro-16-(p-fluorophenoxy)-17,18,19,20-tetranor-PGE$_2$, a compound according to claim 49, wherein R$_1$ is hydrogen.

51. 2,2-Difluoro-16-(p-fluorophenoxy)-17,18,19,20tetranor-PGE$_2$, methyl ester, a compound according to claim 49, wherein R$_1$ is methyl.

52. A compound according to claim 45, wherein s is one and T is chloro.

53. 2,2-Difluoro-16-(p-chlorophenoxy)-17,18,19,20-tetranor-PGE$_2$, a compound according to claim 52, wherein R$_1$ is hydrogen.

54. 2,2-Difluoro-16-(p-chlorophenoxy)-17,18,19,20-tetranor-PGE$_2$, methyl ester, a compound according to claim 52, wherein R$_1$ is methyl.

55. A compound according to claim 45, wherein s is 0.

56. 2,2-Difluoro-16-phenoxy-17,18,19,20-tetranor-PGE$_2$, a compound according to claim 55 wherein R$_1$ is hydrogen.

57. 2,2-Difluoro-16-phenoxy-17,18,19,20-tetranor-PGE$_2$, methyl ester, a compound according to claim 55, wherein R$_1$ is methyl.

58. The compound according to claim 1, wherein M$_1$ is

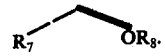

* * * * *

UNITED STATES PATENT AND TRADEMARK OFFICE
CERTIFICATE OF CORRECTION

PATENT NO. : 4,056,556

DATED : November 1, 1977

INVENTOR(S) : Udo F. Axen

It is certified that error appears in the above-identified patent and that said Letters Patent are hereby corrected as shown below:

Column 2, line 56 (claim 16), "16phenoxy" should read -- 16-phenoxy

Column 4, line 1 (claim 40), "16methyl" should read -- 16-methyl --; line 9 (claim 43), "$PGE_2$, methyl ester, a compound" should read -- $PGE_2$, a compound --; line 19, "17,18,19,20tetranor" should read -- 17,18,19,20-tetranor --; line 29 (claim 51), "17,18,19,20te" should read -- 17,18,19,20-te --.

Signed and Sealed this

Eleventh Day of July 1978

[SEAL]

Attest:

RUTH C. MASON
Attesting Officer

DONALD W. BANNER
Commissioner of Patents and Trademarks